(12) United States Patent
Bergmann et al.

(10) Patent No.: US 7,015,003 B1
(45) Date of Patent: Mar. 21, 2006

(54) RECEPTOR BINDING ASSAYS AND REAGENT KIT FOR DETECTING TSH RECEPTOR AUTOANTIBODIES

(75) Inventors: Andreas Bergmann, Berlin (DE); Joachim Struck, Berlin (DE); Nils Morgenthaler, Berlin (DE); Wolfgang Weglöhner, Berlin (DE); Jörg-Michael Hollidt, Berlin (DE)

(73) Assignee: B.R.A.H.M.S Aktiengesellschaft, Hennigsdorf (DE)

( * ) Notice: Subject to any disclaimer, the term of this patent is extended or adjusted under 35 U.S.C. 154(b) by 0 days.

(21) Appl. No.: 09/381,032

(22) PCT Filed: Jan. 13, 1999

(86) PCT No.: PCT/EP99/00159

§ 371 (c)(1),
(2), (4) Date: Dec. 17, 1999

(87) PCT Pub. No.: WO99/36782

PCT Pub. Date: Jul. 22, 1999

(30) Foreign Application Priority Data

Jan. 15, 1998 (DE) ................................ 198 01 319

(51) Int. Cl.
*G01N 33/53* (2006.01)
*G01N 33/537* (2006.01)
*G01N 33/557* (2006.01)
*G01N 33/542* (2006.01)

(52) U.S. Cl. ............... 435/7.1; 435/7.93; 435/7.94; 435/7.95; 436/517; 436/518

(58) Field of Classification Search ........... 435/7.1, 435/7.93–7.95, 7.92; 436/517–518
See application file for complete search history.

(56) References Cited

U.S. PATENT DOCUMENTS 5,614,363 A * 3/1997 Cone et al.
5,814,461 A * 9/1998 Bergmann et al.

FOREIGN PATENT DOCUMENTS

WO 95/06258 3/1995
WO WO-95/06258 A1 * 3/1995
WO 98/26294 6/1998

OTHER PUBLICATIONS

Morgenthaler NG et al, Binding of antithyrotropin receptor autoantibodies in Graves' disease serum to nascent, in vitro translated thyrotropin receptor: ability to map epitopes, Feb. 1996, J Clin Endocrinol Metab 81(2):700-6.*
Morris JC., Structure-function studies of the human thyrotropin receptor. Inhibition of binding of labeled thyrotropin (TSH) by synthetic human TSH receptor peptides, May 1993, J Biol Chem 268(15):10900-5.*
Stryer et al, 1988, in Biochemistry, Third Edition, W. H. Freeman and Company/New York, pp. 31-33.*
Harlow et al, 1988, in Antibodies A Laboratory Manual, p. 25-26, pp. 553-593.*
Kuby et al, 1994, Immunology, Second edition, pp. 86-96.*
Colman et al, 1994, A structural view of immune recognition by antibodies, pp. 33-36.*
Vitti et al, Acta Med Austriaca 23(1-2): 52-6, 1996.*
Nicholson et al, J Mol Endocrinol 16(2): 159-70, 1996.*
Chemical Abstracts, vol. 127, No. 1, Jan. 5, 1998 Columbus, Ohio US; Abstract No. 679865 XP002103277 siehe Zusammenfasung & W.B. Minich et al.: "Expression of a functional tagged human thyrotropin receptor in hela cells using recombinant vaccinia virus" Experimental and Clinical Endocrinology and Diabetes, Bd. 105, Nr. 5, 1997, Seiten 282-290 New York NY USA.

* cited by examiner

*Primary Examiner*—Christina Chan
*Assistant Examiner*—Phuong Huynh
(74) *Attorney, Agent, or Firm*—Mayer Brown Rowe & Maw LLP (57) ABSTRACT

Improved receptor assays for the detection of thyroid stimulating hormone receptor (TSHR) autoantibodies are described which use immobilized, affinity-purified rTSHR preparations as specific binders. This format, as well as novel measures for neutralizing pathologically increased human TSH (hTSH) levels in the sera, e.g., by the addition of anti-hHSH antibody, and/or eliminating the influence of anti-bovine TSH antibody, result in increased assay reliability and open up the possibility of preparing the assay constituents in a ready to use and/or well-standardized form for automatic processing and/or convenient marketing.

10 Claims, 4 Drawing Sheets

Standard TRAK-CT curve using acridinium ester

RECEPTOR BINDING ASSAYS AND REAGENT KIT FOR DETECTING TSH RECEPTOR AUTOANTIBODIES

CROSS-REFERENCE TO RELATED APPLICATIONS

This application is a §371 national stage filing of PCT/EP99/00159, filed Jan. 13, 1999.

BACKGROUND OF THE INVENTION

1. Field of the Invention

The present invention relates to improved receptor binding assays for the determination of TSH receptor autoantibodies (TSH-auto-ab) which occur in thyroid autoimmune diseases, in particular in Graves' disease.

2. Description of the Related Art

It is known that numerous diseases in which the thyroid is involved are autoimmune diseases in which autoantibodies against molecular structures of the thyroid are formed and, in association with the disease, begin to act as autoantigens. The most important known autoantigens of the thyroid are thyroglobulin (Tg), thyroperoxidase (TPO) and in particular the TSH receptor (TSHR) (cf. Furmaniak J et al., Autoimmunity 1990, Vol. 7, pages 63–80).

The TSH receptor is a receptor which is localized in the thyroid membrane and to which the hormone TSH (thyroid-stimulating hormone or thyrotropin) secreted by the pituitary gland binds and thus induces the secretion of the actual thyroid hormones, in particular of thyroxine. The TSH receptor belongs to the receptor family comprising the G-protein-coupled glycoprotein receptors with a large amino-terminal extracellular domain, to which the LH/CG receptor and the FSH receptor also belong. The chemical structure of the TSH receptor, i.e. of the sequence of the DNA coding for it and for the amino acid sequence, derivable therefrom, of the receptor itself, was determined at the end of 1989 (cf. Libert F. et al., Biochem. Biophys. Res. Commun. 165: 1250–1255; Nagayama Y. et al., Biochem. Biophys. Res. Commun. 165: 1184–1190; cf. also EP-A-0433509 or WO-A-91/09121; and WO-A-91/09137; WO-A-91/10735 and WO-A-91/03483; furthermore Yuji Nagayama & Basil Rapoport, in: Molecular Endocrinology, Vol. 6 No. 2, pages 145–156, and the literature cited therein).

It is generally known that stimulating autoantibodies which are formed against the TSH receptor and interact with it so that the thyroid is stimulated play a role in the thyroid autoimmune disease known as Graves' disease, which is manifested as thyroid hyperfunction (hyperthyroidism). The determination of autoantibodies against the TSH receptor is thus of considerable clinical importance for the diagnosis of Graves' disease.

TSHR-auto-ab have been determined to date in biological samples essentially by methods based on two principles (cf. for example Morgenthaler N. G. et al., J Clin Endocrinol Metab 81: 3155–3161 (1966)):

In cell stimulation tests, the presence of stimulating TSHR-auto-ab which are frequently denoted in the literature by the abbreviation TSI (TSI=thyroid stimulating immunoglobulins), is manifested by the fact that specific functions of suitable cells which have natural or recombinant TSHR in their cell membrane and come into contact with an autoantibody-containing sample are triggered or enhanced by stimulation, in particular the formation of cAMP (cyclic adenosine monophosphate). In these tests also referred to as bioassays, the stimulating effect is measured selectively but the measurement is extremely complicated and therefore not very suitable for routine clinical diagnosis.

Alternatively, autoantibodies can also be determined using competitive receptor binding assays, in particular radioreceptor assays, for example with the use of the TRAK-Assay® from B.R.A.H.M.S Diagnostica GmbH. For the determination of TSH receptor autoantibodies (TSHR-auto-ab), this conventional method is used in such a way that the autoantibodies to be determined and originating from a serum sample are allowed to compete in the liquid phase with a radiolabelled bovine TSH ($^{125}$I-bTSH) for the binding sites of a solubilized porcine TSH receptor (porc. TSHR) (cf. Southgate, K. et al., Clin. Endocrinol. (Oxford) 20, 539–541 (1984); Matsuba T. et al., J. Biochem. 118, pages 265–270 (1995); EP 719 858 A2; product information on the TRAK-Assay® from B.R.A.H.M.S Diagnostica GmbH). To determine the $^{125}$I-bTSH bound to the porc. TSHR preparation, the solubilized porc. TSHR used is separated from the liquid phase by means of a precipitating reagent and subsequent centrifuging step after the incubation is complete. The receptor-bound $^{125}$I-bTSH is determined by measuring the radioactivity bound in the sediment. Since the determination is based on a competition between $^{125}$I-bTSH and the autoantibodies to be determined for common binding sites on the porc. TSHR, all those autoantibodies, and only those autoantibodies, which actually compete with bTSH are detected in this method. Such competing autoantibodies capable of inhibiting the TSH binding are also referred to in the literature as TBII (TBII=thyrotropin-binding inhibitory immunoglobulin), and the extent of their activity is also stated as a percentage of so-called TBII activity.

The competitive radioreceptor assays known to date for the detection of TSH receptor autoantibodies have various disadvantages which are attributable to the quality or availability of the assay components used, to the abnormalities which occur in the sera of individual patients and may falsify the results of the measurements in the known assays and to the fact that the binding capability of TSH receptor preparations is generally very sensitive to changes in the receptor or in the biomolecules bound by it. The binding of biomolecules of a peptide or protein nature, for example hormones or autoantibodies, to receptors is as a rule very complicated, and the formation of a specific bond between receptor and biomolecule is very much more sensitive to structural changes, in particular of the receptor, than is the case with a conventional antigen/antibody binding pair, which forms the basis of most immunoassays in which receptors do not play a role. Attempts to immobilize and/or to label the TSH receptor have to date generally led to structural changes which greatly impair the functionality of the receptor. As a consequence of this, there have to date been scarcely any reworkable descriptions of a practical implementation of numerous basic assay types which are available in immunoassays with the use of antibody/antigen binding for the case of receptor binding assays for the determination of TSHR-auto-ab, so that such other assay types cannot yet be used in practice for the TSHR-auto-ab determination. This applies in particular to those assay types in which immobilized binding partners are employed and the concentration of a tracer bound to a solid phase is determined directly at the end of the measurement, or in which bulky molecules such as enzymes, enzyme substrates or a chemiluminescent label, are used for labelling. Since the measurement of a tracer bound to a solid phase is the basis of most automatic assay apparatuses for series measurements, the known assays for the determination of TSH receptor autoantibodies have not to date been feasible on such automatic apparatuses.

The patent DE 43 28 070 C1 describes a type of receptor binding assay which is based on the coated tube technique and in which the difficulty of the preparation of labelled or immobilized functional receptor preparations is circumvented by binding to the solid phase components of a competing reaction system which to some extent represents a "shadow" of the actual receptor binding reaction. However, the disclosed principle of the method has proved too complicated and therefore not very practicable for providing assays for routine clinical diagnosis. The general statement in said patent on the problem of receptor binding assays in general and of those for the determination of TSH receptor autoantibodies in particular are hereby expressly incorporated by reference.

EP-B-0 488 170 discloses cell-free receptor binding tests in which recombinant fusion receptors comprising an amino-terminal receptor protein and a carrier protein, in particular the constant part (Fc) of the heavy chain of an immunoglobulin, are used, which fusion receptors have been coupled to a solid phase by means of an antiserum or of a monoclonal antibody. The receptors discussed do not belong to the class of the high molecular weight G-protein-coupled glycoprotein receptors. Furthermore, immobilization by binding a carrier protein which is the Fc part of an immunoglobulin is not very suitable for receptor binding assays with the aid of which autoantibodies are to be determined, since the autoantibodies themselves belong to the immunoglobulins and can bind to the immobilization system.

Certain disadvantages of the conventional assays are also associated with the fact that reactants of different animal origins, i.e. stabilized porcine TSHR preparations in combination with labelled bTSH, were used for the determination of human TSHR-auto-ab. It is true that said assay components are distinguished by good mutual binding and permit detection of, for example, about 80% to 90% of the human TSHR-auto-ab occurring in Graves' disease. However, the clinical value which is reduced compared with 100% detection of the TSHR-auto-ab to be detected is presumably also due at least partly to the fact that the autoantibodies occurring in patients' sera are directed against the human TSHR but are determined on the basis of their binding to a porcine TSHR preparation. In spite of the basic availability of human TSHR preparations produced by a recombinant method (rhTSHR), such rhTSHR have not yet been used in clinical assays since any expected advantages were cancelled out by numerous new practical disadvantages. In particular, there has to date been just as little possibility as in the case of the porc. TSHR of using a functional, natural rhTSHR in assays in a form bound to a solid phase (immobilized) or in labelled form.

The publications W. B. Minich, M. Behr and U. Loos, Exp Clin Endocrinol Diabetes 105, 282–290 (1997) and "70th Annual Meeting of the American Thyroid Association", 15.19.10.1997, Abstract No. 89, and W. B. Minich, J. D. Weymayer, U. Loos, Thyroid, Vol. 8, 3–7 (1998) (in print) disclose that it is possible to immobilize a recombinant human fusion TSHR by means of a peptide residue attached by genetic engineering and to use said fusion TSHR in this form in TSHR-auto-ab determinations. A corresponding summarizing disclosure is also to be found in the non-prior-published International Patent Furthermore, EP-A 0 719 858 describes a method for the preparation of a functional rhTSHR with the aid of a myeloma cell line. The application mentions in general, speculative form the possibility of producing monoclonal antibodies using the rhTSHR polypeptide prepared, and proposes using such antibodies inter alia for immobilizing rhTSHR and making use thereof in the determination of TSHR-auto-ab. However, neither the actual preparation and selection of such monoclonal antibodies are described, nor is it shown concretely that the proposal actually makes it possible to immobilize the rhTSHR without loss of functionality with the optionally obtainable monoclonal antibodies and to use it in this form in the determination of TSHR-auto-ab. The disclosure of EP-A 719 858 is to this extent not reworkable. Monoclonal antibodies are not mentioned in the parent scientific publication (Matsuba et al., J. Biochem. 118, pages 265–270 (1995)).

After the molecular structure of the TSH receptor had been determined, monoclonal and polyclonal antibodies against complete rhTSHR polypeptides, against the N-terminal extracellular part (comprising 398 amino acids without the signal peptide) of such receptors and against conjugates of shorter receptor peptide partial sequences were prepared by numerous working groups with the aim of determining the TSH receptor epitopes responsible for the TSH binding and the antibody binding (cf. for example N. G. Morgenthaler et al., J Clin Endocrinol Metab 81: 3155–3161 (1996); Seetharamaiah G S et al., Endocrinology 134, No. 2, pages 549–554 (1994); Desai R K et al., J. Clin. Endocrinol. Metab. 77: 658–663, 1993; Dallas J S et al., Endocrinology 134, No. 3, pages 1437–1445 (1994); Johnstone A P et al., Mol. Cell. Endocrinol. 105 (1994), R1–R9; Seetharamaiah G S et al., Endocrinology 136, No. 7, pages 2817–2824 (1995); Nicholson L B et al., J. Mol. Endocrinol. (1996) 16, pages 159–170; Ropars A et al., Cell. Immunol. 161, pages 262–269 (1995); Ohmori M et al., Biochem. Biophys. Res. Commun. 174, No. 1 (1991), pages 399–403; Endo T. et al., Biochem. Biophys. Res. Commun. 181, No. 3 (1991), pages 1035–1041; Costagliola S et al., Endocrinology 128, No. 3, pages 1555–1562, 1991; Marion S et al., Endocrinology 130, No. 2, pages 967–975 (1992); J. Sanders et al., J. Endocrinol. Invest. 19 (Suppl. No. 6); 1996, and further publications cited in said publications). The various antibodies were tested for their binding behaviour with respect to the TSH receptor or partial sequences thereof produced by a recombinant method and in particular with respect to their ability to interfere with the binding of TSH to various forms or fragments of the TSH receptor. Since the various polyclonal or monoclonal antibodies had been produced by immunization of different animals and/or with the use of recombinant material from different expression systems and in addition TSH receptors produced by recombinant methods and of various origins or peptide fragments thereof were frequently used in the binding tests, and since furthermore it was found that the glycolization and/or correct folding of the receptor peptide was likely to be decisive for the binding of numerous antibodies, the epitope structure of natural TSH receptors and the epitope-specific binding behaviour of the autoantibodies occurring the polyclonal antibody populations of human sera have not yet been fully determined.

In the publication by Dallas J S et al., Endocrinology 134, No. 3, pages 1437–1445 (1994), for example, a partial recombinant TSH receptor which is prepared with the aid of the Baculovirus/insect cell expression system and has the amino acids of the extracellular domain of the human TSH receptor without the N-terminal signal peptide is used for immunizing rabbits, and specific antibody fractions are obtained from the resulting immunoglobulin fractions by affinity chromatography with the use of synthetic peptides each having about 20 amino acids. Said specific antibody fractions are then investigated, inter alia, with regard to their suitability for blocking the binding of TSH to a solubilized porcine TSH receptor in a commercial receptor binding assay. The antibodies showed no stimulatory activity.

The publication by Seetharamaiah G S et al., Endocrinology 136, No. 7, pages 2817–2824 (1995) describes how the same partial recombinant TSH receptor as in the above publication was used for immunizing mice and for preparing monoclonal antibodies against individual epitopes of the TSH receptor by standard techniques. A similar procedure is described in Nicholson L B et al., J. Mol. Endocrinol. (1996) 16, pages 159–170.

According to Seetharamaiah G S et al., Endocrinology 134, No. 2, pages 549–554 (1994), a partial recombinant TSH receptor prepared as above is subsequently folded and then tested with respect to its suitability for binding radiolabelled bTSH. For this purpose, it is reacted in the liquid phase with radiolabelled bTSH. To separate the resulting complex as quantitatively as possible from the reaction mixture, an antibody which was produced by immunizing rabbits with a conjugate of a partial peptide, containing the amino acids 357 to 372 of the complete TSH receptor sequence, and had been found not to inhibit the binding of bTSH to the unfolded partial recombinant TSH receptor is then added as part of a precipitation system (Desai R K et al., J. Clin. Endocrinol. Metab. 77: 658–663, 1993). The added antibody or the complexes which contained it and bound radiolabelled bTSH is or are then precipitated with the aid of protein A, which binds unspecifically to every antibody. Under the experimental conditions, the binding of protein A to the receptor-bound antibody does not appear to impair the simultaneous bTSH binding.

In the earlier, non-prior-published Patent Application 196 51 093.7, a practically feasible competitive solid-phase receptor assay for the determination of TSHR-auto-ab is furthermore described for the first time, in which assay the TSHR-auto-ab to be determined and labelled bTSH or optionally also a labelled monoclonal antibody are allowed to compete for binding sites of a solubilized TSHR, and the TSHR complexes formed are bound to a solid phase by means of an immobilized monoclonal antibody. In the Application 196 51 093.7, those monoclonal antibodies which recognize relatively short amino acid sequences of the TSHR are used in combination with crude solubilized porcine or optionally also recombinant TSHR preparations. The immobilization of the TSHR complexes is effected in the embodiment with the aid of an affinity gel to which a sequential monoclonal anti-hTSHR-mab has been bound. The focal point of the teaching of the Application 196 51 093.7 is the increase in the clinical value of the TSHR-auto-ab determination, in particular with the use of the conventional crude solubilized TSHR preparations. However, the content of said Application, in particular concerning possible assay variations, is hereby expressly incorporated by reference.

A particular method for obtaining anti-hTSHR-mab is furthermore described by S. Costagliola and G. Vassart in J. Endocrinol. Invest. 20 (Suppl. to no. 5), Abstract 4 (1997). According to this method, immunization of mice for the purpose of antibody formation is effected not with a peptide antigen but by intramuscular injection of a DNA plasmid construct coding for the hTSHR. In this way, novel monoclonal antibodies having high affinity to the natural hTSHR are obtained. This technique has proved very valuable and is also used in the present application, in particular for the preparation of anti-hTSHR-mab which recognize conformational epitopes.

In addition, it may be noted that the knowledge obtained with antibodies against recombinant TSH receptors or parts thereof led to the proposal to use, for the determination of receptor autoantibodies, a third principle, known per se, in the form of an immunoprecipitation assay, in which a preparation of an extracellular part of a recombinant TSH receptor labelled by incorporation of $^{35}$S-methionine is used as a reagent for the precipitation. In one such assay, there is no selectivity either for TSI or for TBII (N. G. Morgenthaler et al., J Clin Endocrinol Metab 81: 700–706 (1996)). However, the preparation of the $^{35}$S-labelled receptor by in vitro translation is extraordinarily complicated and expensive, and there are no measuring apparatuses which are suitable for a routine clinical measurement of the radiation emitted by $^{35}$S. The method is therefore unsuitable as a method of measurement for routine clinical diagnosis.

SUMMARY OF THE INVENTION

It is the object of the present invention to provide a receptor binding assay for the determination of TSH receptor autoantibodies, which assay does not have the described disadvantages of competitive receptor binding assays of the prior art and is of high clinical value.

In particular, it is the object of the present invention to provide an improved receptor binding assay for the determination of TSH receptor autoantibodies, in which the TSH receptor complexes formed from the reactants of the assay are obtained directly in a form bound to the solid phase, so that an automated procedure for such receptor binding assays is also possible.

In particular, it is furthermore the object of the present invention to design improved receptor binding assays for the detection of TSH receptor autoantibodies in such a way that specific disturbances of the measurement by abnormal serum constituents are effectively ruled out and optimum binding of the reactants of the assay is ensured.

It is furthermore the object of the present invention to provide the reagent kits required for carrying out such improved receptor binding assays in routine clinical diagnosis.

Said objects are achieved in the case of a competitive receptor binding assay according to the precharacterizing clause of claim 1 at least partly by radioreceptor assays which have the features reproduced in the characterizing clause of claim 1.

In the investigations leading to the achievement of the above-mentioned object, various knowledge which relates to the binding of TSH, in particular bTSH, to rhTSHR and is used in the tests described below in the experimental part was furthermore obtained.

Such advantageous embodiments of the improved receptor binding assays according to the invention are also described in the subclaims, in particular in conjunction with the more detailed explanations in the description below.

The object of providing a reagent kit for realizing the present invention is achieved by a preferred reagent kit which contains at least one each of the constituents (i) and (ii) according to claim 13.

In the introduction and in the following part of this Application, the reagents or analytes/biomolecules used are characterized as a rule by various abbreviations, which are always to be understood as having the following meanings, unless, as an exception, something different is evident to a person skilled in the art from the specific context. The use of the specific data is intended to permit an exact description of the tests and measurements carried out but does not mean that the results and conclusions described apply only to the special case described. Rather, much of the information obtained is clearly recognizable in its general meaning for a person skilled in the art.

Explanations of the abbreviations used:

TSH=Thyroid stimulating hormone (thyrotropin). If the abbreviation TSH is used without additions, it does not refer to a specific product but instead the binding or function of the hormone is discussed in general form.

bTSH=Bovine TSH (i.e. obtained from cattle). Preparation which is used as a tracer in assays for the determination of autoantibodies against the TSH receptor (in particular radioiodinated or, as described herein, labelled with a chemiluminescent label, in particular an acridinium ester label; however, it is within the scope of the present invention to use any other known label).

$^{125}$I-bTSH=Radioiodinated bTSH used as a competitor. In connection with the description of assays from B.R.A.H.M.S Diagnostica GmbH, $^{125}$I-bTSH represents in particular a product as obtained according to DE 042 37 430 C1 or EP 0 668 775 B1 and forming a component of the TRAK-Assay® from B.R.A.H.M.S Diagnostica GmbH.

hTSH=Human TSH. Occurs in the serum/plasma of healthy people only in very low concentrations of 0.2–4 mU/l. In sera of patients suffering from hypothyroidism, however, the hTSH concentration may be significantly increased. The disturbances of autoantibody measurements which are caused by raised hTSH levels (more than 20 mU/l) are discussed in the description and eliminated by special measures. The current state of knowledge on the structure of hTSH is summarized in Grossmann et al., Endocrine Review, Vol. 18, 1997, pages 476–501.

TSHR=The TSH receptor, a glycoprotein receptor anchored in the thyroid membrane. If the abbreviation TSHR is used without further additions, it does not refer to a specific product and instead the function of the receptor or its involvement in the binding is being discussed in general form.

porc. TSHR=Solubilized crude receptor preparation obtained by extraction from thyroids of pigs (porcine). Used as a specific binder in the radioreceptor precipitation assays of the prior art for the determination of autoantibodies against the TSHR (conventional TRAK-Assay® from B.R.A.H.M.S Diagnostica GmbH).

rhTSHR=Genetically engineered (recombinant) polypeptide which has the amino acid sequence of a naturally occurring human TSHR at least to an extent such that it can be regarded as a "functional human TSHR receptor", which means that it behaves to a significant extent like the naturally occurring human TSHR regarding the binding of autoantibodies against the TSHR or of hTSH. If the abbreviation rhTSHR is used without further additions, it does not refer to a specific product, i.e. rhTSHR can represent any recombinant complete, more or less glycosylated polypeptide, a partial sequence of a sufficient length or a genetically engineered fusion product (as described, for example, in the International Patent Application PCT/EP97/06121). Without further explanations, a product denoted simply by "rhTSHR" is present as a crude detergent-solubilized membrane preparation, i.e. in the form as obtained by conventional solubilization, with the use of detergents, of membranes of the cells used for expressing the recombinant polypeptide.

rTSHR(imm)=rhTSHR preparation bound selectively to a solid phase (immobilized). The binding can—as described more exactly below in the description—take place via a suitable antibody but, in the case of fusion products, can also take place via a particular peptide residue, e.g. a biotin radical. The solid phase may be the wall of a test tube (coated-tube or CT technique) but may also be a suitable suspended solid.

rhTSHR(imm)*=Immobilized rhTSHR bound via a selected anti-hTSHR-mab to a solid phase (see above) and purified in bound form by washing to remove foreign constituents. Also referred to as "affinity-purified rhTSHR".

Ab=Antibody

TSHR-auto-ab=Autoantibodies against the TSH receptor which are detectable in biological samples, in particular human serum or plasma. The detection of stimulating TSHR-auto-ab of this type (in the literature also abbreviated to TSI=thyroid stimulating immunoglobulins) is particularly important for the diagnosis of Graves' disease. A commercial assay (radioreceptor assay) for the determination of TSHR-auto-ab is the TRAK-Assay® from B.R.A.H.M.S Diagnostica GmbH.

Anti-hTSHR-mab=Monoclonal antibody which binds to rhTSHR. Without further explanations, it may be of a sequential nature with regard to its binding behaviour, as described, for example, in the prior Application DE 196 51 093.7 but it can also be of conformational nature. The selection of specific anti-hTSHR-mab of this type for realizing the assays according to the invention is described in more detail in the Application. If special anti-hTSHR-mab are used in the experiments, they are characterized by a number explained in the application. If a slightly modified, less specific abbreviation (e.g. simply anti-TSHR-ab) is used, it is intended to avoid a restriction, unnecessary at this point, to monoclonal antibodies against the human TSHR.

Anti-bTSH-ab=Antibodies of unknown origin which occur in human sera or plasma, react with bTSH with formation of immune complexes and thus influence the binding of bTSH to the assay components and the measured result obtained (cf. Y. Ochi et al., Acta Endocrinologica (Copenh) 1989, 120, 773–777; S. Sakata et al., J. Endocrinol. Invest. 14: 123–130, 1991; T. Inui, Thyroid, Vol. 6: 259–299, 1996).

As explained in the introductory part, the known competitive receptor binding assays, all of which are designed as radioreceptor assays, contain the following basic assay components in addition to the required standards and buffer solutions:

(i) A TSH receptor preparation as a specific binder, in the conventional assays in particular a solubilized natural porcine TSH receptor (porc. TSHR) obtained from pigs' thyroid membranes, (ii) $^{125}$I-bTSH, which competes with TSH receptor autoantibodies from a serum sample or plasma sample (TBII) for common binding sites on the TSH receptor used and (iii) an agent for separating the resulting TSHR complex from the liquid reaction solution, which in the case of the conventional assay is the precipitating agent polyethylene glycol (PEG).

A feature which distinguishes the present invention from the known prior art is that it was shown experimentally that it is possible to use a functional rhTSHR (i.e. a human recombinant TSH receptor) in affinity-purified form which is selectively mobilized on a solid phase, instead of the solubilized TSHR preparation, without the binding capability of the affinity-purified rhTSHR (rhTSHR(imm)*) with respect to the TSHR-auto-ab to be determined and labelled bTSH being significantly impaired. With this knowledge, the precondition was created for developing a receptor binding assay for the determination of TSHR-auto-ab which is even further improved in many respects in which the determination of the amount of the bound labelled bTSH can be carried out directly in the form bound to the solid phase. In the more exact investigation of the binding of bTSH to the novel TSHR preparation, additional valuable knowledge was obtained and has been used in the invention and its preferred embodiments. Further details are given in the experimental part. The most important aspects of said further knowledge are:

1. The interfering effect of pathologically high hTSH concentrations in individual patients' samples can be eliminated by adding specific commercial antibodies (anti-hTSH-ab) to the sample-containing measuring solution, which antibodies selectively bind hTSH and do not cross-react with the bTSH used as competitor.
2. If the determination is carried out as a "two-step determination" by allowing labelled bTSH to react in a downstream step with a previously formed complex of TSHR-auto-ab separated from the original measuring solution and with the affinity-purified rhTSHR(imm)*, the possible presence of anti-bTSH-ab in the patient's sample can no longer have a disturbing effect.
3. The new knowledge mentioned above under 2. makes it possible to carry out the reaction with bTSH in the second assay step with an exactly standardizable bTSH reagent free of serum.
4. The presence of third substances, for example of specific serum constituents which could be characterized as constituents of a serum fraction which contains only substances having molecular weights of <10,000 d, is advantageous for the binding of bTSH to rhTSHR preparations. Some of the low molecular weight substances which improve the binding, in particular dissolved inorganic ions, could be more exactly identified. It was possible to show that, however, inorganic ions do not have the stated effect when complexing by EDTA, i.e. bound in firm complexes.

Because the method according to the invention permits binding of the TSHR-auto-ab and of the labelled competitor bTSH from the test solution directly to an affinity-purified rhTSHR(imm)* bound to a solid phase, not only is the measurement of the signal obtained simplified in practice in the desired sense compared with a precipitation assay, but the assay design can be fundamentally changed by converting from a one-step assay (a single test solution obtained by successive pipetting without intermediate solid-liquid separation) to a two-step assay in which the reaction of rhTSHR (imm)* with the sample and the reaction with the labelled competitor bTSH are carried out in two successive steps separated from one another by a solid-liquid separation.

Plastics surfaces, in particular the walls of plastic test tubes for the CT technique, microparticles, magnetic particles, filters, polymer gel materials and other known solid-phase carriers may be used as solid-phase carriers for the affinity-purified rhTSHR(imm)*. By means of the method according to the invention, the TSHR-auto-ab determination can also be automated. Thus, the assay design can be adapted in such a way that it can be carried out on known automated systems (cf. for example Elecsys system from Boehringer Mannheim or ACS 180 system from Chiron). In the case of such automated systems, the samples are pipetted into receptor-coated test tubes, and incubated, the liquid reaction mixture is then filtered off with suction or decanted, and a second solution with the labelled bTSH, e.g. $^{125}$I-bTSH, is added, in the course of an automatic procedure. After the prescribed incubation, the customary final solid-liquid separation is then effected, after which the signal can be measured, optionally after signal triggering by addition of suitable reagents. The pipetting sequence stated by way of example for a two-step assay is variable and can be replaced, for example, by the pipetting sequence of a one-step assay (2.1.1), optionally also without prior immobilization of the rTSHR.

Below, the present invention is explained in more detail in its various aspects on the basis of specific embodiments and experimental results with reference to eight Figures. Reference is expressly made to the general explanations in connection with the experiments described, as part of the disclosure of the present invention.

BRIEF DESCRIPTION OF THE DRAWING

The Figures show the following in the form of various diagrams.

DESCRIPTION OF THE PREFERRED EMBODIMENTS

The following descriptions of preparation and measurement experiments are organized as follows:
1. Preparation/selection of the assay components used;
2. Incubation protocols for 2 measuring methods with the use of labelled bTSH and affinity-purified rhTSHR (imm)* according to a one-step and two-step technique; and
3. Results of the measurement of TSHR-auto-ab in standard samples or patients' sera with the use of test tubes according to the invention which have been coated with affinity-purified rhTSHR(imm)*, according to the principle of competition with labelled bTSH.

1. Materials 1.1 Production of a Preparation of a Crude Solubilized rhTSHR

In order to express the rhTSHR in high yield in a mammalian cell line, a human chronic leukaemia cell line was transfected in a stable manner analogously to conventional procedures with a bicistronic vector which contained the cDNA for the complete human TSH receptor and said leukaemia cell line was cultured in suspension culture. Exploratory experiments with other systems showed that the specific expression system is not critical and essentially the same success can also be achieved using the expression system described in EP-A-0 719 858 and operating with myeloma cell lines or with the vaccinia virus/HeLa cell expression system described in PCT/EP97/06121. With the cells of warm blooded animals described in EP-B1-0 433 509, too, it was possible to obtain the rhTSHR in a quality which permitted implementation of the teaching of this Application. On the basis of the knowledge to date, however, it is important that the expression of the human TSH receptor is effected in mammalian cells, preferably used cells being those which can be cultured in suspension and give high rhTSHR yields.

Cells which contained the expressed rhTSHR in their cell membrane were digested to obtain a solubilized rhTSHR preparation, as described in more detail in S. Costagliola et al., J. Clin. Endocrinol. Metab. 75: 1540–1544 (1992), all operations being carried out at 4° C. In each case $10^9$ cells were digested in 50 mM HEPES (4-(2-hydroxyethyl)-1-piperizinethanesulphonic acid; pH 7.5). The digestion was carried out with the aid of a Potter homogenizer (from B Braun Melsungen A G) by moving the piston up and down ten times at a speed of 900 rpm. The material obtained was centrifuged at 100,000 g for 30 min. The sediment obtained was rehomogenized in 20 ml of buffer (10 mM HEPES; 2% Triton-X-100; pH 7.5) with a repetition of the procedure described and was again centrifuged for 30 min at 100,000 g. The supernatant obtained, which contained the crude solubilized rhTSHR preparation, was divided into portions and stored at −80° C. until further use.

1.2 Preparation of Labelled bTSH 1.2.1 $^{125}$I-bTSH $^{125}$I-bTSH was prepared as described in the patents DE 42 37 430 C1 and EP 0 668 775 B1.

1.2.2 bTSH Chemiluminescence-Labelled with Acridinium Ester bTSH chemiluminescence-labelled with acridinium ester was prepared as follows: 100 µg of bTSH (50–60 IU/mg of protein; in 20 mM sodium phosphate; pH 7.0) were reacted with 10 µl of acridinium ester (from Behringwerke A G, Marburg; cf. EP 0 257 541 B1; 1 mg/ml in acetonitrile) for 15 min at room temperature and then prepared by means of HPLC on a Waters Protein Pak SW 125 column (mobile phase: 0.1 M ammonium acetate; pH 5.5; flow rate: 0.6 ml/min). All fractions of the column outflow with a UV absorption at 280 nm and 368 nm were collected. The pooled protein fraction was stored at −80° C. until further use in receptor binding assays.

1.3 Standards

Standards for the determination of TSHR-auto-ab were prepared by mixing TSHR-auto-ab-positive sera having a known antibody content and autoantibody-free human sera, in each case adjusted to 0.05% sodium azide and stored at 4° C. until further use. The calibration of the standards was carried out using the TRAK-Assay® from B.R.A.H.M.S Diagnostica GmbH.

1.4 Anti-hTSHR-mab Production and Selection

A group of monoclonal mouse antibodies against the TSH receptor was produced using various immunization methods as described in the literature (J. S. Dallas et al., Endocrinology 134, No. 3, pages 1437–1445 (1994)—immunization with extracellular receptor domain prepared recombinantly by the Baculovirus method; L. B. Nicholson et al., J. Mol. Endocrinol. (1996) 16, pages 159–190—immunization with the extracellular receptor domain produced in procaryotic cells or by the Baculovirus method; Johnstone A. P. et al., Mol. Cell. Endocrinol. 105 (1994), R1–R9—immunization with various recombinant TSHR polypeptides; immunization with synthetic receptor peptide conjugates; J. Sanders et al., J. Endocrinol. Invest. 19 (Suppl. to No. 6): 1996, Abstract 33—immunization with fusion proteins produced in E. coli and containing TSHR fragments; and in particular S. Costagliola and G. Vassart, J. Endocrinol. Invest. 20 (Suppl. to No. 5): 1997, Abstract No. 4—immunization of mice with a DNA construct).

The selection and production of individual clones were carried out as in the respective publications cited or by generally known methods for the preparation of monoclonal antibodies. The purification of the various monoclonal antibodies obtained was carried out by means of protein A affinity chromatography. Eleven of the anti-hTSHR-mab obtained were tested for their ability to bind a previously produced complex of rhTSHR and $^{125}$I-bTSH.

For this purpose, in a first step, $^{125}$I-bTSH (36,000 cpm total activity) was incubated with the solubilized rhTSHR (about 1 ng) in a total volume of 100 µl which contained 50 mM HEPES; pH 7.5; 10,000 IU/ml of heparin; 10 mM $CaCl_2$; 0.2% Triton X-100 (cf. the experimental results below). To check the unspecific binding, 0.1 IU/ml of unlabelled bTSH was added in separate batches. After incubation for one hour at room temperature, the determination of the bTSH/rhTSHR binding was carried out by three different methods:

1.4.1 Isolation of Previously Formed bTSH/rhTSHR Complexes by Means of PEG Precipitation (Obtaining of a Reference Value)

2 ml of PEG precipitation reagent from the TRAK-Assay® from B.R.A.H.M.S Diagnostica GmBH were added to the above reaction solution. Thereafter, centrifuging was carried out (10 min at 2000 g), the supernatant was decanted and the radioactivity remaining in the sediment was measured. Quantitative precipitation of the resulting bTSH/rhTSHR complex was found.

1.4.2 Immunoprecipitation of Previously Formed bTSH/rhTSHR Complexes with the anti-hTSHR-mab to be Tested In each case 10 µg (in 50 µl of the buffer used for producing the bTSH/rhTSHR complex) of the respective anti-hTSHR-mab to be investigated were added to the above reaction solution and, after incubation for one hour, 100 µl of protein A (from HENNING-Test® anti-TPO from B.R.A.H.M.S Diagnostica GmbH) were added as precipitation reagent, incubation was carried out for 15 min and finally 2 ml of phosphate-buffered saline solution (PBS) were added, after which centrifuging was carried out (50 min at 2000 g). By adding protein A, all antibodies contained in the reaction mixture are precipitated. The bTSH/rhTSHR complex is precipitated only to the extent that it has bound to the antibody to be investigated. Accordingly, the radioactivity to be found in the centrifugation segment represents the amount of bTSH/ rhTSHR complex which was bound by the respective anti-hTSHR-mab.

1.4.3 Binding of Previously Formed bTSH/rhTSHR Complexes with the aid of Immobilized anti-hTSHR-mab (CT Technique)

To immobilize the respective anti-hTSHR-mabs, polystyrene tubes coated with goat anti-mouse antibodies (kit component of the DYNOtest® TBG from B.R.A.H.M.S Diagnostica GmbH) were each incubated with 100 ng of the anti-hTSHR-mab to be investigated, with the code numbers 1 to 11, in 200 µl of PBS for 2 h at room temperature. Thereafter, 2 ml of PBS were added and the liquid tube content was decanted. The coated test tubes obtained were then incubated directly with the reaction solution described above, which contained the bTSH/rhTSHR complex (100 µl), incubation being effected for 1 h with shaking at 300 rpm. Thereafter, the test tubes were washed with two 2 ml portions of wash buffer (10 mM HEPES; 0.1% Triton X-100; pH 7.5) and the radioactivity fixed on the surface of the test tubes was measured. The radioactivity value obtained in the case of the PEG precipitate, minus the separately determined unspecific binding: (B-UB)=10,490–433 cpm=10,057 cpm, is used as complete binding of the bTSH/rhTSHR complex. This value corresponds to a B/T value (bound radioactivity to total radioactivity used) of 28%.

The binding values obtained in the testing of the anti-hTSHR-mab 1–11 according to the methods 1.4.3 and 1.4.4 are shown in Table No. 1 below, the radioactivity of the sediment of the PEG precipitation according to 1.4.1 being taken as the reference value with 100%. In the case of all data shown, the unspecific bindings, i.e. the radioactivity in the presence of an excess of unlabelled bTSH, have been subtracted.

TABLE 1

| Antibody number | Immuno-precipitation with 10 µg ab % binding * | CT assay with 100 ng ab % binding * | Radio-activity in the Western blot ** | Epitope *** |
|---|---|---|---|---|
| 1 | 40.9 | 4 | + | 22–35 |
| 2 | 11 | <2 | + | 32–54 |
| 3 | 12.8 | <2 | + | 287–301 |
| 4 | 10.8 | <2 | + | 334–343 |
| 5 | 28 | 5.1 | + | 354–359 |
| 6 | 13.4 | 3.5 | + | 352–361 |
| 7 | 41.7 | 8 | + | 361–381 |
| 8 | <2 | <2 | + | 402–415 |
| 9 | 99 | 47.6 | – | 3D |
| 10 | 103 | 16.2 | – | 3D |
| 11 | 104 | 20.6 | – | 3D |

Explanations for Table 1:
* The values are each stated as percentage precipitation of the maximum precipitatable bTSH/rhTSHR complex (100% = precipitation in the case of PEG precipitate).
** Determined as described by Johnstone, A. P. et al., Mol. Cell. Endocrinol. 105 (1994), R1–R9;
*** cf. the following experiments for mapping the binding sites of anti-hTSHR-mab (mouse)

1.4.4 Mapping the Binding Sites of anti-hTSHR-mab (Mouse)

The principle of mapping involves finding the synthetic partial peptide sequences of hTSHR to which the respective antibody to be investigated binds.

1.4.4.1 Preparation of a Group of Peptides which Correspond to Partial Sequences of the hTSHR.

Partial sequences of the hTSHR sequence, each of which comprises 13 amino acids, were prepared in the form of synthetic peptides. The partial sequences were chosen so that the total hTSHR sequence is reproduced and in each case two successive sequences overlap by nine amino acids (e.g. peptide 1: amino acids 1 to 13; peptide 2: amino acids 4 to 16; peptide 3: amino acids 7 to 19, etc.). The synthetic peptides were then synthesized alongside one another in the form of about 2×2 mm "spots" on cellulose paper. This method of peptide preparation is an established method and is commercially available, inter alia, from JERINI Biotools GmbH, Berlin. Reference may be made to the following publications for explanations: R. Frank, Peptides 1990, 151–152; A. Furga et al., Int. J. Peptide Protein Res. 37, 1991, 487–493; R. Frank, Tetrahedron Vol. 48, No. 42, 9217–9232, 1992. The paper with the peptide spots was incubated for 1 h at room temperature in 20 ml of so-called "blocking solution" (blocking solution: 50 mM Tris; pH 8.0; 50 mM NaCl; 0.05% Tween 20; 5% sucrose; 1× Blocking Reagent from Cambridge Research Biochemicals, No. SU-07-250).

1.4.4.2 Characterization of the anti-hTSHR-mab 1 to 11

20 µl of a solution which contained one of the anti-hTSHR-mab 1–11 to be investigated in a concentration of 10 µg/ml were then added to the cellulose paper prepared according to 1.4.4.1. Incubation was then carried out for 3 h at room temperature with swirling, after which decanting was effected. The paper was washed 6 times with 5 ml of "wash buffer" (wash buffer: 50 mM Tris; pH 8.0; 50 mM NaCl; 0.5% Tween). 20 ml of the above blocking solution which contained 5 µl of goat anti-mouse IgG alkaline phosphatase conjugate from BIORAD, No. 1721015, in the freshly diluted state were then added. Incubation was then carried out again for 2 h at room temperature with swirling. Decanting was then effected again, and the paper was washed 6 times with 5 ml of the above wash buffer.

By adding a substrate solution which reacts with the antibody-bound alkaline phosphatase, those peptides to which the respective investigated anti-hTSHR-mab had bound were finally identified. The substrate solution used for visualization was obtained as follows: 6 mg of Nitro Blue Tetrazolium (SIGMA No. N-6876) were dissolved in 6 ml of dimethylformamide. 2.5 mg of 5-bromo-4-chloro-3-indolyl phosphate (SIGMA No. B-8503) were dissolved in 0.5 ml of dimethylformamide. 4 ml of the Nitro Blue Tetrazolium solution described, 400 µl of the 5-bromo-4-chloro-3-indolyl phosphate solution and 160 µl of a 1 M $MgCl_2$ solution were dissolved in 36 ml of substrate solution from the ELItest® Anti-TG from B.R.A.H.M.S Diagnostica GmbH, No. 944638. The solution obtained was added to the cellulose paper.

After 20 min at room temperature, those peptide spots to which the investigated anti-hTSHR-mab had bound had been stained violet owing to the substrate reaction. The peptides corresponding to the stained spots were identified in this manner as binding sites of the anti-hTSHR-mab investigated. The binding sites of the investigated anti-hTSHR-mab determined in this manner are shown in the last column of the above Table 1. The anti-hTSHR-mab with the numbers 9, 10 and 11 bound to none of the peptides taken, which is to be regarded as an indication that these antibodies 9, 10 and 11 are those which recognize exclusively conformational structures of the rhTSHR. Said "conformational" anti-hTSHR-mabs 9, 10 and 11 had been obtained by the method of S. Costagliola and G. Vassart according to the publication in J. Endocrinol. Invest. 20 (Suppl. 2, No. 5) 1997, Abstract 4, by immunization of mice with a hTSHR-DNA construct.

In the experiments, described above under 1.4.3, for the binding of the bTSH/rhTSHR complex with the various anti-hTSHR-mab, it was found, as shown in Table 1, that most antibodies, although used in a considerable excess (10 µg of antibodies compared with about 1 ng of rhTSHR), were not able completely to precipitate the bTSH/rhTSHR complex. Only the antibodies 9, 10 and 11 permit complete precipitation of said bTSH/rhTSHR complex and, in mapping, these proved to be "conformational" antibodies, i.e. those which do not recognize specific peptide sequences but exclusively conformational structures. For the development of a coated-tube assay according to the invention, in which TSHR-auto-ab are to be determined with the aid of an immobilized rhTSHR, said conformational antibodies 9, 10 and 11 which gave the highest binding were therefore preferably considered.

However, it should be emphasised that, although said conformational antibodies are very particularly suitable for immobilizing rhTSHR, the remaining anti-hTSHR-mab 1–8 also functioned, but very low binding levels were obtained. Such monoclonal antibodies can be used, alone or optionally also in the form of a mixture of two or more anti-hTSHR-mab, for the binding of rhTSHR with presentation of different hTSHR epitopes, in order, in the context of the disclosure in Patent Application 196 51 093.7, optionally to detect additional autoantibody subpopulations in the test and thus optionally to increase the clinical value if this should prove desirable.

1.5 Immobilization and Affinity Purification of the rhTSHR to Obtain Test Tubes for a Coated-Tube Assay for the Determination of TSHR-auto-ab A crude solubilized rhTSHR preparation according to 1.1 was diluted with 100 mM HEPES; 0.5% Triton X-100; 0.5% bovine serum albumin (BSA); pH 7.5 until about 30% binding of the $^{125}$I-bTSH was obtained with the use of the reagents of the commercial TRAK-Assay® from B.R.A.H.M.S Diagnostica GmbH in the case of the PEG precipitation carried out according to the working instructions of said assay.

For the production of coated tubes, 100 ng of the above anti-hTSHR-mab No. 9 were added to 200 μl of rhTSHR dilution obtained, and the resulting solution was introduced into polystyrene tubes whose walls had been coated with goat anti-mouse antibodies (mouse IgG binding capacity about 100 ng) and was incubated at 4° C. for 20 h.

The test tubes used were those which were part of the DYNOtest® TBG kit from B.R.A.H.M.S Diagnostica GmbH.

After the incubation, the tubes were filled with 2 ml of wash buffer (10 mM HEPES; 0.1% Triton X-100; pH 7.5), decanting was carried out and drying was then effected in a vacuum dryer for 4 h. By means of the wash step, undesired impurities were removed, so that the tubes had a highly affinity-purified rhTSHR (rhTSHR(imm)*) on their walls. The tubes were used in the determinations described below. They were stored at 4° C. until they were used.

2. Pipetting and Incubation Protocols

To investigate the binding behaviour of bTSH to the novel affinity-purified rhTSHR receptor preparation (rhTSHR(imm)*) in more detail, various control experiments were carried out using the test tubes obtained as described above under 1.5 and containing the affinity-purified rhTSHR(imm)*, one of the following pipetting/incubation protocols being used:

2.1 One-Step Assay
1. Pipette the sample (patient's serum, standard serum or null standard serum; 100 μl) in rhTSHR(imm)*-coated test tubes.
2. By means of a pipette, add $^{125}$I-bTSH or acridinium ester-labelled bTSH, in each case in 100 μl of 100 mM HEPES; 20 mM EDTA; 0.5 mM N-ethylmaleimide (NEM); 0.1 mM leupeptin; 1% BSA; 0.5% Triton X-100; 5 μg anti-hTSH-ab (cf. 3.2); pH 7.5.
3. Incubate for 2 h with shaking (300 rpm) at room temperature.
4. Wash with two 2 ml portions of washbuffer, decant.
5. Measure the radioactivity fixed to the wall of the test tube in a γ-counter or initiate the luminescence reaction and measure the chemiluminescence light yield with a suitable luminometer, e.g. Berthold LB952.

2.2 Two-Step Assay
1. Pipette buffer (200 μl; 100 mM HEPES; 20 mM EDTA; 0.5 mM NEM; 0.1 mM leupeptin; 1% BSA, 0.5% Triton X-100; 5 μg anti-hTSH-ab; pH 7.5) into a rhTSHR(imm)*-coated test tube.
2. Pipette the sample (patient's serum, standard serum or null standard serum; 100 μl).
3. Incubate for 2 h with shaking (300 rpm) at room temperature.
4. Pipette 2 ml of wash buffer (cf. above), decant.
5. Pipette 200 μl of buffer solution containing a labelled bTSH ($^{125}$I-bTSH or acridinium ester-labelled bTSH) (10 mM HEPES; 10,000 IU/ml heparin; 10 mM calcium chloride; 1% BSA; 0.1% Triton X-100; pH 7.5).
6. Incubate for 1 h with shaking (300 rpm) at room temperature.
7. Wash the tubes twice with 2 ml of wash buffer where $^{125}$I-bTSH was used, or four times with 1 ml of wash buffer where acridinium ester-labelled bTSH was used.
8. Measure the radioactivity fixed to the wall of the test tube in a γ-counter or initiate the luminescence reaction and measure the chemiluminescence light yield with a suitable luminometer, e.g. Berthold LB 952.

3. Determination of TSHR-auto-ab in Patients' sera 3.1 Two Step Assay for the Determination of TSHR-auto-ab and its Advantages Knowledge confirmed by various control experiments makes it possible to carry out the TSHR-auto-ab determination with the use of rhTSHR(imm)*-coated test tubes as a two-stage assay in which, in the second step, a serum-free and therefore readily standardizable labelled bTSH preparation is used. The use of labelled bTSH in a second assay step in the absence of all sample constituents not bound to the immobilized rhTSHR certainly rules out falsification of the measured values by anti-bTSH-ab which occur to a significant extent in various patients' sera (cf. above explanation regarding anti-bTSH-ab).

According to the conventional assay protocol, such anti-bTSH-ab in patients' sera lead to "falsely" reduced measured values of the TSHR-auto-ab concentration since such antibodies are coprecipitated together with the bound labelled bTSH in the PEG precipitation and simulate an excessively low binding of TSHR-auto-ab.

In the measurement according to the above-mentioned one-step assay protocol, the presence of anti-bTSH-ab leads to "falsely" increased measured values since insufficient labelled bTSH is bound to the walls of the test tube.

In the two-step method, there is no contact between the sample and the labelled bTSH, so that anti-bTSH-ab no longer represent an interfering factor, especially when the second step is carried out in the absence of serum. The two-step variant is therefore currently preferred for the procedure with TSHR-auto-ab.

3.2 Prevention of Falsification of Measurements by Pathologically Increased hTSH Concentrations in Patients' sera.

Using a human TSHR preparation as a receptor binder, it was intended to test whether the results of the determination of TSH-auto-ab with the use of the above-mentioned coated test tubes can be disturbed by the presence of hTSH in patients' samples. hTSH usually occurs in human sera in extraordinarily low concentrations which do not present problems. However, it is known that pathologically increased hTSH concentrations can occur in the hypothyroid state.

Increasing amounts of hTSH (Boehringer Mannheim, Germany) were added to a serum freed from hTSH (Skandibodies, USA) to obtain defined sample solutions. The sera obtained were measured as samples according to the above two-step assay protocol (2.2).

Figure 1:
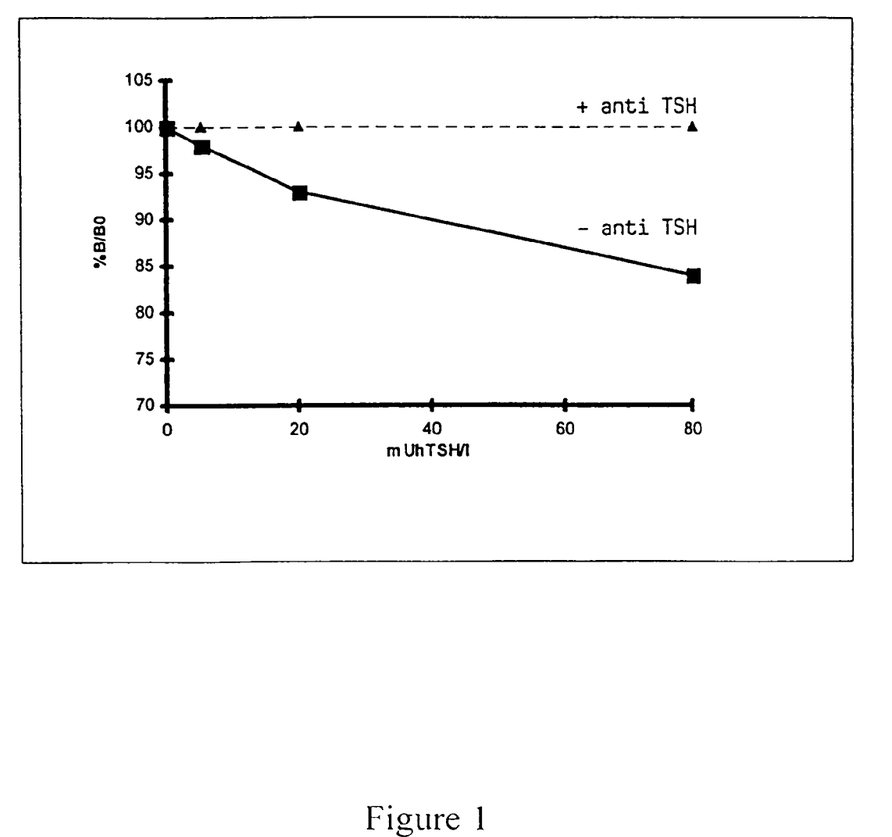
FIG. 1:
The dependence of the binding of $^{125}$I-bTSH to an affinity-purified rhTSHR(imm)* which had been treated in an upstream reaction step with serum containing increasing amounts of hTSH (curve—■—), a part of the sera (curve—▲—) additionally containing an excess of a selective anti-hTSH-ab.

As shown in FIG. 1, the binding of the labelled bTSH is influenced by competition with the hTSH in the case of pathologically high hTSH concentrations.

By adding an hTSH antibody to the sample solution, the effect of the presence of hTSH in the sample is eliminated. A suitable hTSH antibody is the commercially available antibody with the Article No. 5404 from Oy Medix Biochemica Ab, Finland. By adding an excess of such an antibody (e.g. 5 µg/test), the effect of increased hTSH concentrations is eliminated. Since said hTSH antibody exhibits no cross-reaction with bTSH, it can be added to the sample solution also in the one-step assay variant (cf. 2.1, step 2.) and leads to the same improvement in the results of the measurements.

3.3 Improved Assay for the TSHR-auto-ab Determination and Testing Thereof in Practice All of the above knowledge thus led to a novel assay for the determination of TSHR-auto-ab in patients' sera or patients' plasma, the reliability of which determination could be tested by measuring a group of patients' sera, the two-step assay incubation protocol (2.2) being used.

3.3.1 Standard Curves

Figure 2:
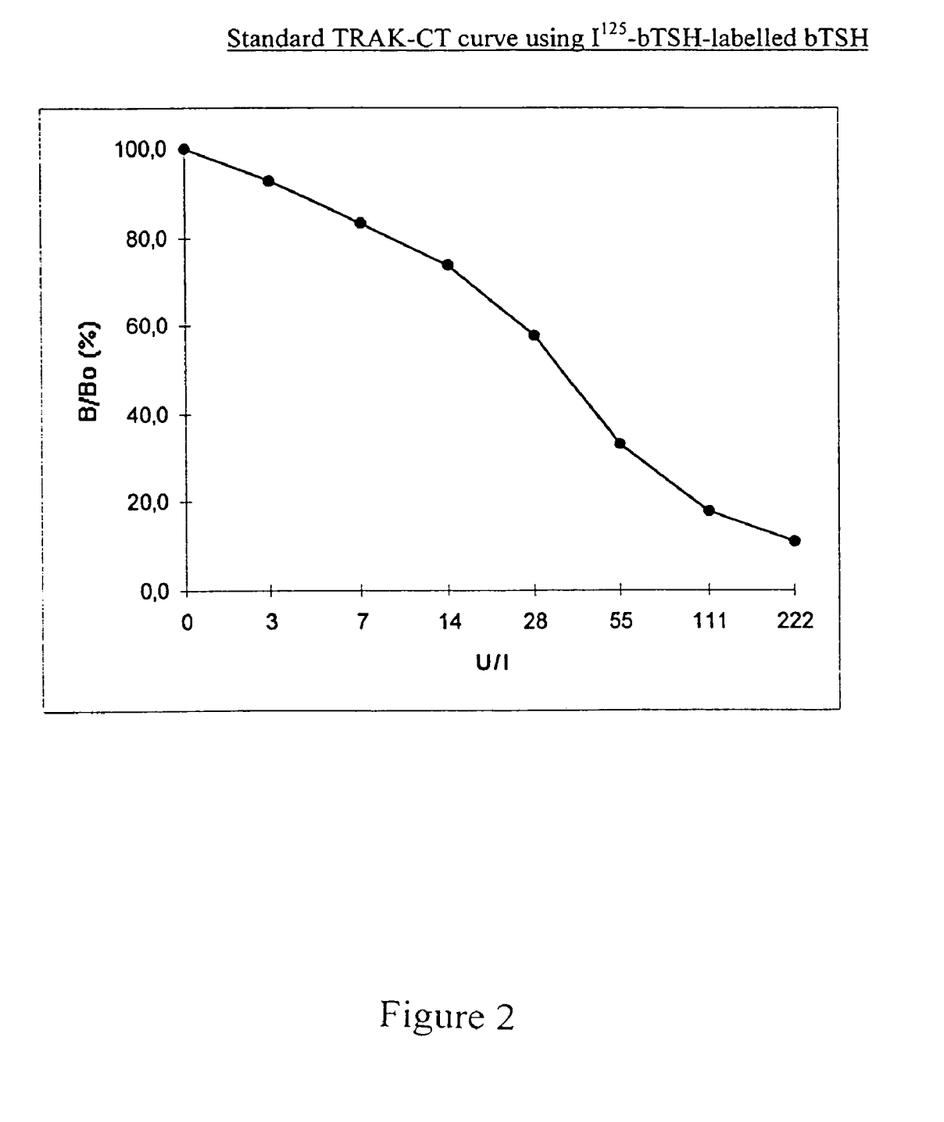
FIG. 2:
The standard curve for the measurement of TSHR-auto-ab with the use of $^{125}$I-bTSH and of an affinity-purified rhTSHR(imm)* in a two-step method.
Figure 3:
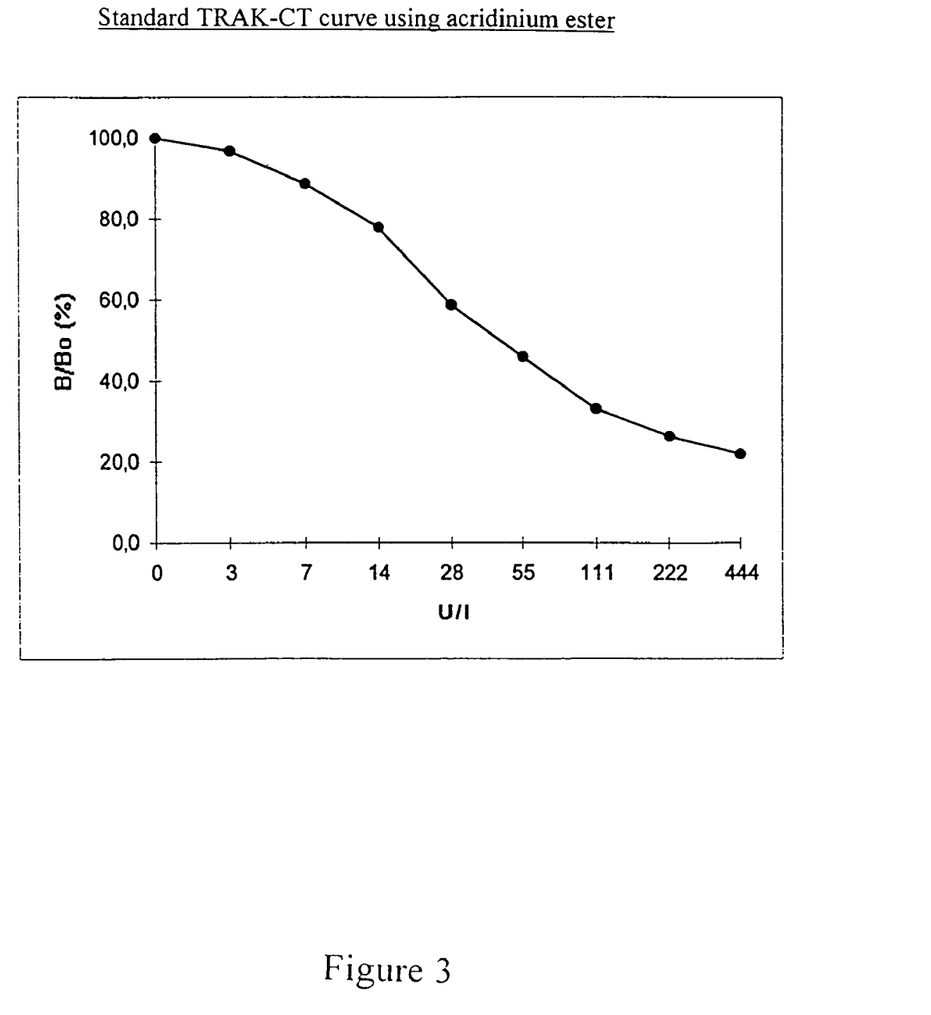
FIG. 3:
The standard curve for the measurement of TSHR-auto-ab with the use of a bTSH chemiluminescence-labelled with an acridinium ester and of an affinity-purified rhTSHR(imm)* in a two-step method.

FIGS. 2 and 3 show the standard curves obtained with the use of the standard according to 1.3 and using $^{125}$I-bTSH (FIG. 2) and acridinium ester-labelled bTSH (FIG. 3). The null standard is a pooled serum of people with a healthy thyroid; standards 400 to 3 are mixtures from pooled sera of people with a healthy thyroid and of patients suffering from Graves' disease. The calibration was carried out using the conventional TRAK-Assay® from B.R.A.H.M.S Diagnostica.

3.3.2 Measurement of Patients' sera

Independently of the type of labelling of the bTSH, TSHR-auto-ab reduce the binding of the labelled bTSH to the surface of the test tubes in a concentration-dependent manner, a substantial positive signal being detectable from only 3 U/l.

Figure 4:
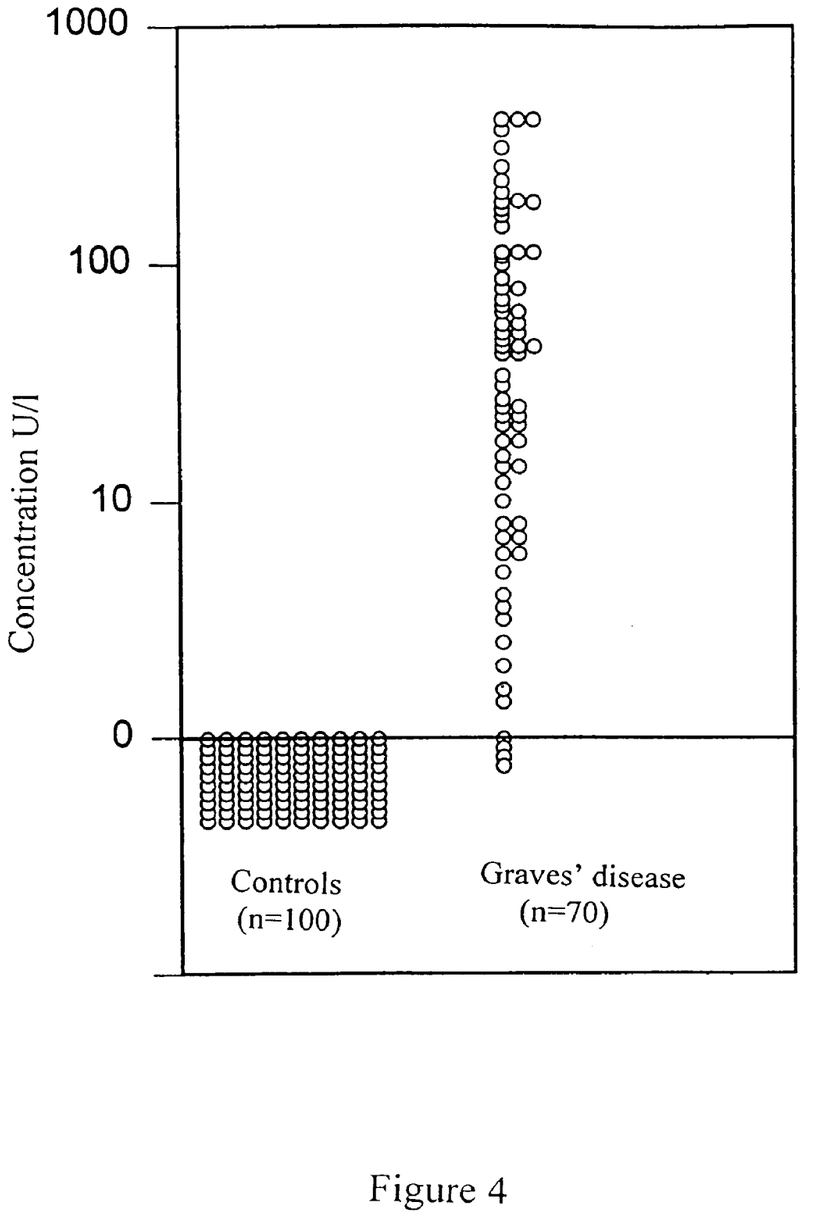
FIG. 4:
The results of the measurement of patients' sera (100 control sera; 70 sera of patients suffering from Graves' disease) by the two-step method with the use of $^{125}$I-bTSH and affinity-purified rhTSHR(imm)*.

According to the two-step assay protocol described (2.1.2), 100 control sera of people with a healthy thyroid and 70 sera of patients suffering from Graves' disease were measured. The results are shown in FIG. 4. A considerable difference between sera of patients with Graves' disease, which contain TSHR-auto-ab, and those from control persons with a healthy thyroid is clearly evident.

The invention permits an improvement in the method for the determination of TSHR-auto-ab both with respect to exclusion of interfering physiological factors which might falsify the results of the measurements in assays to date and in particular from the practical point of view. Based on the teaching in the present invention, it is possible for the first time to prepare all or at least most reagents for carrying out such a method in ready-to-use form and to make said reagents available to users (for example in the form of precoated test tubes and standardized, serum-free tracer reagents).

What is claimed is:

1. A method for the determination of TSH receptor autoantibodies comprising:

(i) reacting a solid phase, comprising an affinity-purified immobilized functional recombinant human TSH receptor, with a liquid biological sample to be assayed for the presence of said autoantibodies;

(ii) separating a reacted solid phase from the liquid biological sample;

(iii) washing the reacted solid phase;

(iv) incubating the reacted solid phase with a buffer solution comprising an amount of labeled bovine TSH for a sufficient time to occupy all the TSH binding sites of the functional recombinant human TSH receptor not occupied by the autoantibodies; and (v) determining the presence and/or amount of the autoantibodies on the basis of the amount of labeled bovine TSH bound to the solid phase;

wherein the functional recombinant human TSH receptor is immobilized to a solid support by a selective monoclonal antibody that recognizes only conformational epitopes of the human TSH receptor and is obtained by immunizing an animal with a DNA plasmid construct encoding the human TSH receptor and washed.

2. A method for the determination of TSH receptor autoantibodies comprising:

(i) reacting a solid phase comprising an affinity-purified immobilized functional recombinant human TSH receptor with a solution prepared from:

a) a serum-containing biological sample to be assayed for the presence of said autoantibodies, and b) a buffer solution containing an amount of labeled bovine TSH for a sufficient time to occupy all the TSH binding sites of the functional recombinant human TSH receptor not occupied by the autoantibodies;

(ii) separating the solution from a reacted solid phase;

(iii) washing the reacted solid phase; and (iv) determining the presence and/or amount of the autoantibodies on the basis of the amount of labeled bovine TSH bound to the solid phase;

wherein the functional recombinant human TSH receptor is immobilized to the solid support by a selective monoclonal antibody that recognizes only conformational epitopes of the human TSH receptor and is obtained by immunizing an animal with a DNA plasmid construct encoding the human TSH receptor and washed.

3. The method according to either claim 1 or claim 2, wherein the solid phase is formed by the walls of test tubes, which are pre-coated with an animal-specific antibody for binding the selective monoclonal antibody against the human TSH receptor.

4. The method according to either claim 1 or claim 2, carried out in an automated form, wherein the solid phase comprises suspended particles that are coated with said selective monoclonal antibody against the human TSH receptor, and wherein by adding the functional recombinant human TSH receptor and the sample a solution containing the suspended solid particles and the receptor is temporarily formed.

5. The method according to claim 1, wherein the labeled bovine TSH is added in a serum-free buffer solution.

6. The method according to either claim 1 or claim 2, wherein step (i) is carried out in the presence of at least one antibody against human TSH that does not cross-react with bovine TSH.

7. The method according to either claim 1 or claim 2, wherein the autoantibodies are receptor-stimulating autoantibodies, whose occurrence in a human serum is characteristic of Graves' disease.

8. The method according to either claim 1 or claim 2, wherein the affinity-purified immobilized functional recombinant human TSH receptor is in the presence of a buffer.

9. The method according to either claim 1 or claim 2, wherein said sample is diluted with a buffer.

10. A method for the determination of TSH receptor autoantibodies comprising:
   (i) reacting a solid phase, comprising an affinity-purified immobilized functional recombinant human TSH receptor, with a liquid biological sample to be assayed for the presence of said autoantibodies;
   (ii) separating a reacted solid phase from the liquid biological sample;
   (iii) washing the reacted solid phase;
   (iv) incubating the reacted solid phase with a buffer solution comprising an amount of labeled bovine TSH for a sufficient time to occupy all the TSH binding sites of the functional recombinant human TSH receptor not occupied by the autoantibodies; and
   (v) determining the presence and/or amount of the autoantibodies on the basis of the amount of labeled bovine TSH bound to the solid phase;
   wherein the functional recombinant human TSH receptor is immobilized to a solid support by a selective monoclonal antibody that:
   a) recognizes only conformational epitopes of the functional human TSH receptor and is obtained by immunizing an animal with a DNA plasmid construct encoding the human TSH receptor; and
   b) does not bind to peptides representing short sequences of the human TSH receptor, but which shows strong binding to the complete functional recombinant human TSH receptor;
   and then washed.

* * * * *